(12) United States Patent
Billiar et al.

(10) Patent No.: US 8,147,428 B2
(45) Date of Patent: Apr. 3, 2012

(54) DEVICE AND METHOD FOR QUANTIFYING EDEMA

(75) Inventors: Kristen L. Billiar, Worcester, MA (US); Raymond M. Dunn, Shrewsbury, MA (US)

(73) Assignees: University of Massachusetts, Boston, MA (US); Worcester Polytechnic Institute, Worcester, MA (US)

( * ) Notice: Subject to any disclaimer, the term of this patent is extended or adjusted under 35 U.S.C. 154(b) by 0 days.

(21) Appl. No.: 11/107,302

(22) Filed: Apr. 15, 2005

(65) Prior Publication Data

US 2006/0030791 A1 Feb. 9, 2006

Related U.S. Application Data

(60) Provisional application No. 60/562,770, filed on Apr. 16, 2004.

(51) Int. Cl.
*A61B 5/103* (2006.01)
*A61B 5/117* (2006.01)

(52) U.S. Cl. ........................ 600/587

(58) Field of Classification Search .......... 600/372, 600/382, 384, 398, 552, 561, 587, 595, 300, 600/306
See application file for complete search history.

(56) References Cited

U.S. PATENT DOCUMENTS

| | | | |
|---|---|---|---|
| 4,159,640 A * | 7/1979 | Leveque et al. .................. 73/81 |
| 4,253,449 A | 3/1981 | Arkans et al. | |
| 4,331,133 A | 5/1982 | Arkans | |
| 4,418,690 A | 12/1983 | Mummert | |
| 4,492,234 A | 1/1985 | Arkans | |
| 4,741,345 A | 5/1988 | Matthews et al. | |
| 4,771,792 A * | 9/1988 | Seale .......................... 600/587 |
| 5,170,570 A | 12/1992 | Mays, Jr. | |
| 5,662,123 A | 9/1997 | Goldmann | |
| 5,788,643 A | 8/1998 | Feldman | |
| 5,843,007 A | 12/1998 | McEwen et al. | |
| 5,957,867 A * | 9/1999 | Lloyd et al. .................. 600/587 |
| 6,017,307 A | 1/2000 | Raines | |
| 6,186,962 B1 * | 2/2001 | Lloyd et al. .................. 600/587 |
| 6,283,916 B1 * | 9/2001 | Leahy et al. .................. 600/300 |
| 6,294,519 B1 | 9/2001 | Oeltgen et al. | |
| 6,315,745 B1 | 11/2001 | Kloecker | |
| 6,409,662 B1 * | 6/2002 | Lloyd et al. .................. 600/300 |
| 6,415,525 B1 | 7/2002 | Watkins | |
| 6,468,237 B1 | 10/2002 | Lina | |
| 6,544,202 B2 | 4/2003 | McEwen et al. | |
| 6,551,252 B2 | 4/2003 | Sackner et al. | |
| 6,577,897 B1 | 6/2003 | Shurubura et al. | |
| 6,632,192 B2 | 10/2003 | Gorsuch et al. | |
| 6,723,051 B2 | 4/2004 | Davidson et al. | |
| 6,740,038 B2 | 5/2004 | Davidson et al. | |
| 2002/0173711 A1 * | 11/2002 | Walton .......................... 600/398 |
| 2003/0220556 A1 * | 11/2003 | Porat et al. .................... 600/407 |

* cited by examiner

*Primary Examiner* — Jeffrey G Hoekstra
(74) *Attorney, Agent, or Firm* — Weingarten, Schurgin, Gagnebin & Lebovici LLP

(57) ABSTRACT

The preferred embodiments of the present invention are directed at a device that provides a reliable, accurate and quantifiable measure of a patient's edema. The device improves on the current method of digital manipulation by evaluating the pitting phenomena in a user-independent manner. The output of the device allows a physician to categorize edema into at least ten different levels of severity. The systems of the present invention provides the ability to distinguish between tissues of varying viscosity.

18 Claims, 4 Drawing Sheets

DEVICE AND METHOD FOR QUANTIFYING EDEMA

CROSS REFERENCE TO RELATED APPLICATIONS

The present application claims the benefit of U.S. Provisional Application No. 60/562,770, filed Apr. 16, 2004. The entire contents of the above application is incorporated herein by reference.

BACKGROUND OF THE INVENTION

Venous Stasis Disease (VSD), characterized by edema, occurs when there is an obstruction and/or incompetence of the venous valves or veins in the arms and legs. Edema, an atypical accumulation of fluid in the interstitial space, is caused by fluid leaking out of the vasculature into the surrounding tissue subsequent to the buildup of pressure in the venous walls. While uncomfortable for the patient and capable of leading to other serious complications, edema can be an indicator of the extent of VSD.

One of the complications resulting from VSD are leg ulcers. If the valves are damaged the blood can backflow causing high pressure in the veins. Under these conditions fluids that are normally retained in the veins leak out, resulting in swelling in the legs. This swelling can prevent oxygen, which is carried in the blood and necessary for the healing process, from reaching the wound site. Compression therapy is often used as treatment with the rationale that if the excess fluid can be squeezed out, oxygen can return and the wound can heal.

Currently, there is no device which is capable of measuring the severity of edema in a feasible, economical and quantifiable way. The most widely used clinical method for assessing the amount of edema is digital manipulation. This assessment is accomplished by pressing into the patient's leg and qualitatively evaluating the degree of pitting. Pitting is the indentation in the swollen tissue that remains following removal of pressure from the edemous area. Due to the altered tissue composition resulting from edema, there is a putty-like consistency to the tissue, and the tissue remains in the indented position for seconds to minutes before returning to its original form. The doctor performing the test assesses the depth of the indention, how much force is required to reach the tibia, for example, how long the tissue takes to return to the original state, and skin quality. The level of edema is described using a ranking system of one to four (slight to severe). Despite the qualitative nature of this technique, it is still considered the state of the art for edema assessment. There is a continuing need to improve the assessment of edema that is reliable and economical.

SUMMARY OF THE INVENTION

The preferred embodiments of the present invention relate to a device that provides a reliable, accurate and quantifiable measure of a patient's edema. The device improves on the current method of digital manipulation by evaluation of the pitting phenomena in a user-independent manner. The output of the device in accordance with a preferred embodiment of the present invention allows a physician to categorize edema into at least ten different severities, for example, thereby improving on digital manipulation's subjective one to four scale. The systems of the present invention provide for the ability to distinguish between tissues of varying viscosity.

The systems and methods of the present invention include a tonometer which can be used as an office device to assess swelling of the extremities, such as the lower leg. It includes an electromechanical or optical sensor that when applied to the swollen region of the leg provides a measure of the tone (i.e., pressure) in the leg. After a region of tissue is compressed for a selected period of time the applied pressure is released. The rate of return or relaxation of the tissue after release of pressure indicates quantitatively the condition of the tissue. The slower the rate of return, the more severe the edema. Thus, the device can provide a quantitative measure of displacement and applied pressure as well as these parameters as a function of time. The pressure in the leg is a function of the amount of edema, for example, which is can be correlated to the amount of oxygen at the wound site. The reading received can be used to determine if compression therapy is a valid treatment and if so, what amount of compression is needed. The patient's healing progress can then be assessed by periodic measurements, for example, weekly to determine if swelling has decreased.

In accordance with an aspect of the present invention, a preferred embodiment of the device is used for assessing compression therapy which is often used to treat leg ulcers. The regions of the leg with the ulcer is wrapped in elastic compression bandages. Several layers of bandages may be necessary to achieve the pressure required to control or inhibit fluid flow in the veins or tissue in and around the ulcer. A preferred embodiment device includes a miniaturized pressure sensor that can measure and monitor the amount of pressure resulting from compressing a region of the leg, for example. This device can be used to accurately gauge the amount of pressure being applied by the bandages for compression therapy.

The tonometer device in accordance with a preferred embodiment of the present invention for assessing edema in the lower extremities is easy to use and can be inexpensively manufactured. It can be sufficiently low power to be run on batteries and can have a wired or wireless connection to a computer or a computer network in a clinic, physician's office or hospital. This device provides an office tool used to determine if compression therapy is a valid treatment for a particular leg ulcer, for example. The device is also an indicator of congestive heart failure as the fluid retained in the peripheral extremities is correllated with the severity of a patient's heart condition.

The foregoing and other features and advantages of the system and method for quantifying edema will be apparent from the following more particular description of preferred embodiments of the system and method as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

The preferred embodiments of the present invention are directed at a device that provides a reliable, accurate and quantifiable measure of a patient's edema. The device improves on the current method of digital manipulation by evaluating the pitting phenomena in a user-independent manner. The output of the device allows the physician to categorize edema into at least ten different severities, thereby improving on digital manipulation's subjective one to four scale.

Figure 1:
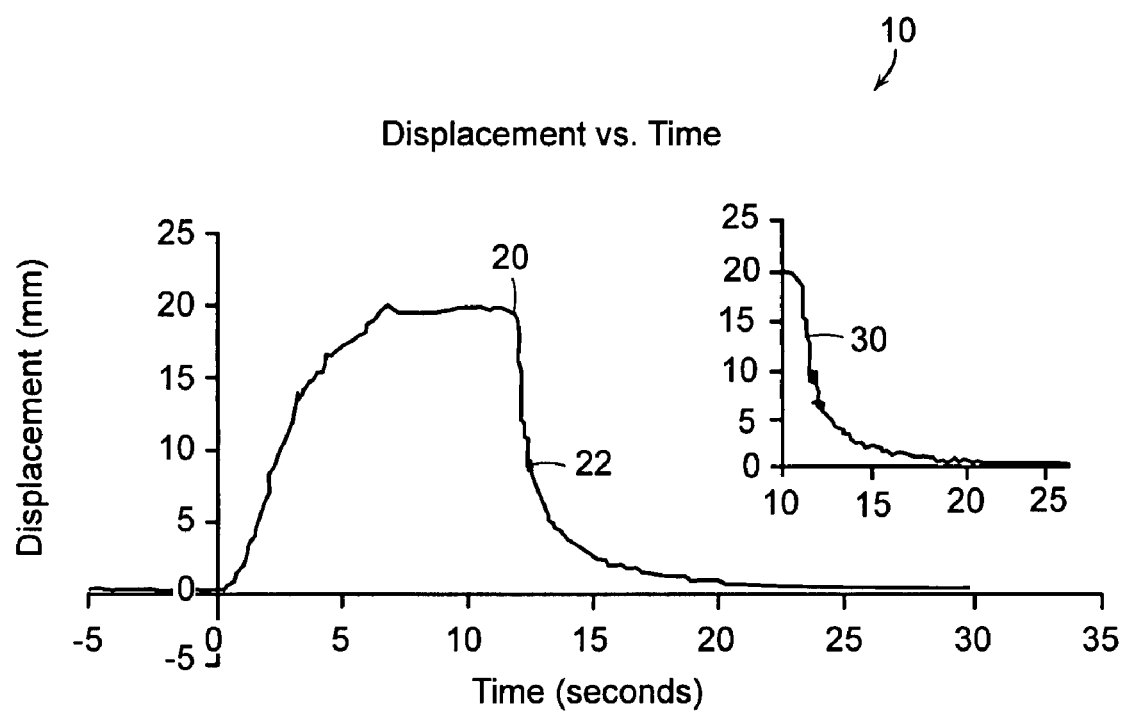
FIG. 1 graphically illustrates displacement into a sample material versus time during measurement of the pitting phenomenon in accordance with a preferred embodiment of the present invention.

During an assessment of pitting, a clinician presses his/her thumb into the tissue, for example, the lower leg. The displacement of the tissue peaks, then as the thumb is released the skin recovers due to the viscoelastic properties of the tissue. These viscoelastic properties, and thus the time-course of the recovery, are dependent upon the severity of edema. FIG. 1 illustrates the displacement if an exemplary material versus time during measurement of the pitting phenomenon. In FIG. 1, indention into the material occurred during the first 7 seconds. The indenting member was then held constant at the maximum depth for 5 seconds. At the twelve second mark, the force was released. The sample material recovered to its original dimensions over the following 20 seconds. The point 22 on the curve represents the "half-time," that is the time that it takes for the material to return to half its original depth which is used as the measure of recovery time in accordance with a preferred embodiment of the present invention. The half time can also be displayed on the relaxation curve only at 30. The relaxation point can be selected by the user to provide a more diagnostically useful indicator depending on the type of condition being evaluated.

In accordance with a device of a preferred embodiment of the present invention, the time it takes for the skin to return half way to its undeformed position is used as the measure of the recovery time and the measure of severity of edema.

Figure 2A:
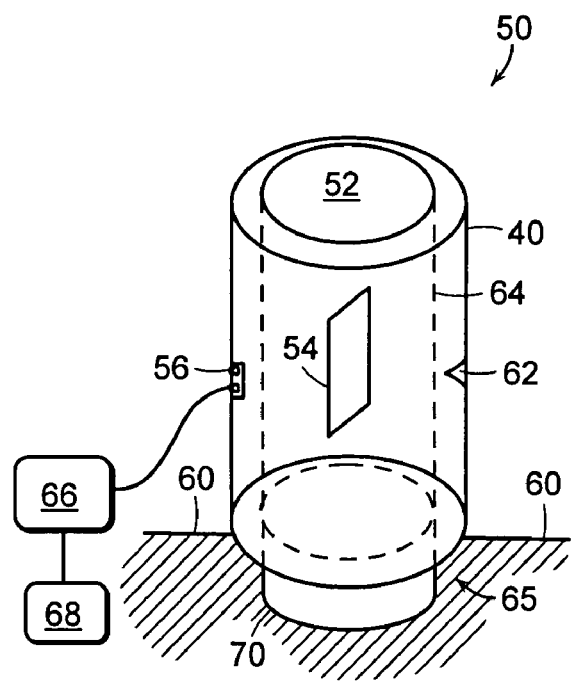
FIGS. 2A and 2B illustrate, schematically, devices used to quantify edema in accordance with a preferred embodiments of the present invention.

FIG. 2A illustrates a schematic of a device 50 in accordance with a preferred embodiment of the present invention. The device 50 in accordance with a preferred embodiment can include two concentric cylinders. The inner cylindrical member 64 acts as the "indenter" or member which moves vertically, and the outer tube 40, the base or housing is stationary. A light emitting diode (LED) or other light source 62 and a matched photoreceptor or detector 56 are attached to the base cylinder. Attached to the inner cylinder is a barrier 54, arranged so as the inner member 64 lowers into the tissue 65 the barrier lowers and gradually blocks the light collected by the detector 56. The barrier 54 can be mounted to an opening in the cylinder 64 that allows light to pass through. The barrier 54 can be made of an opaque material such as plastic that has a linear or non-linear variation in thickness to provide a variable transmissiveness. This arrangement results in a voltage change which is a function of the depth of the member 64. The detector is connected to an amplification and filter circuit 66. The output voltage can be displayed on a display 68, an oscilloscope or collected by a data acquisition board for processing and display at a later time period. Other types of electro-mechanical sensors such as capacitive sensors, Hall effect sensors, LVDTs, etc. can also be used to measure the response of the tissue to displacement.

In operation, the thumb can depress upper surface 52, for example, presses the member 64 into the tissue 60, causing the barrier 54 to block a portion of the light from the LED 62 to the detector 56. The base 40 is used to stabilize the device and mount the detector, light source 62, cylinder and barrier 54.

To evaluate a device in accordance with a preferred embodiment of the present invention, measurements were taken to assess the ability of the device to distinguish between three materials with varying viscoelastic properties. The materials chosen were three pieces of viscoelastic foam (Latex Mattress Center, San Francisco): one dry, one saturated with vegetable oil, and the last saturated with 5W-40 motor oil. These three materials represent and are indicative of a range of severities of edema. Each sample responded differently in terms of the force required to indent the material and rate of return after being released.

The device was situated to rest upon the foam surface. The operator then pressed the member 64 into the foam using his thumb. The force was applied for a three second interval and then released. An oscilloscope (Tektronix, TDS210) was used to view a time versus voltage output as the member 64 returned and the half time was calculated. The output value of the device was also recorded.

To validate the difference in viscoelastic properties between the materials by an independent measurement system, the recovery from indentation was also measured using a Laser Displacement System (LDS) (LK-081, Keyence Corporation, Woodcliff Lake, N.J.), and the output value recorded.

For the validation measurements using the LDS, the average half time ($\pm$SD) for the foam infused with motor oil was 2.88$\pm$0.51 seconds, with vegetable oil was 2.21$\pm$0.38 seconds, and dry was 1.09$\pm$0.43 seconds. This data demonstrates the substantial increase in half-time of the material as the viscosity of the fluid in the foam increases.

Figure 3:
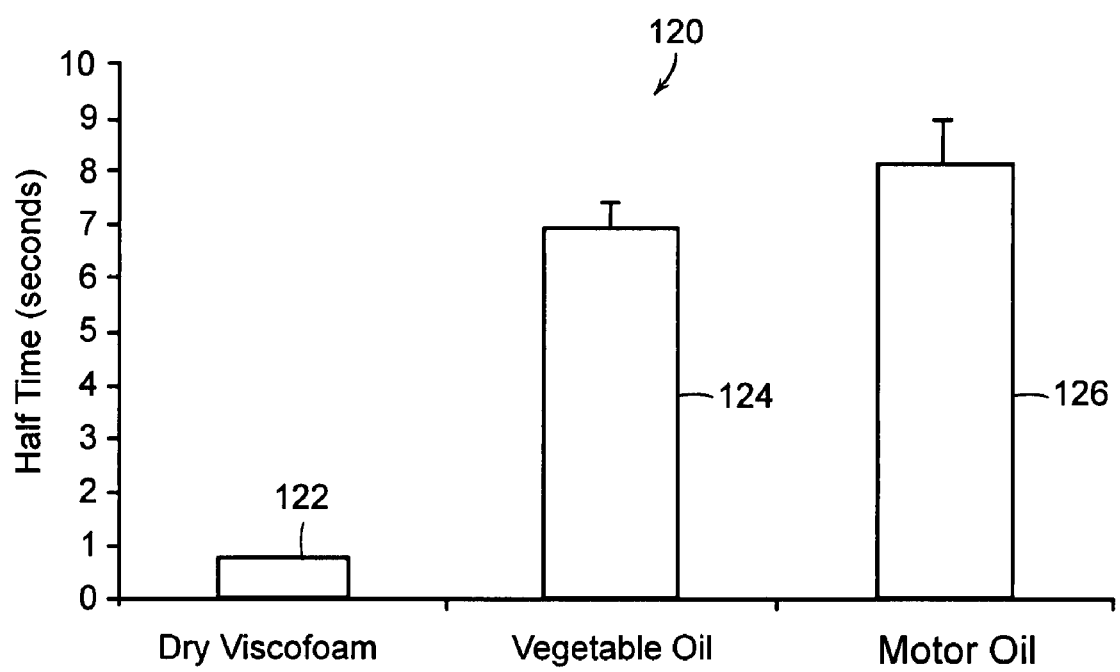
FIG. 3 illustrates data collected using a system to measure edema in accordance with a preferred embodiment of the present invention.

The half-time data recorded using the device in accordance with a preferred embodiment of the present invention is shown in FIG. 3. Half-time to recovery from indentation data is measured using the device. The measurement data shows clear distinctions between the three foam samples, two of which were saturated with liquids of increasing viscosity. These measurements indicate that the device can be used to distinguish between different severities of edema which produce similar changes in viscoelastic response to tissues in patients with venous statis disease.

In the validation measurement, the device demonstrates its ability to clearly differentiate between materials with viscoelastic properties in the range of mild to moderate edema. This result indicates that the methodology described herein may be useful for assessing the severity of edema in patients with VSD. The methods and systems in accordance with a preferred embodiment of the present invention improve upon current methods for assessing edema in that it is inexpensive, portable, easy to use, and provides a quantitative measure.

Figure 2B:
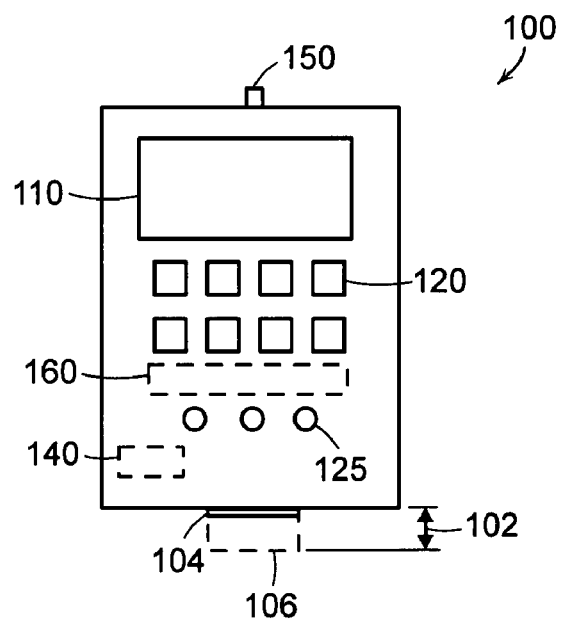

The variability of the half-life values for each material was very small (coefficient of variation <10%). However, the arrangement of the barrier and optical elements in the device in accordance with a preferred embodiment of the present invention produces a non-linear response which limits the useful range of the device. The highest intensity light is directly between the LED and the detector. As the barrier is lowered, the amount of light blocked increases. In another preferred embodiment in accordance with a preferred embodiment of the present invention, the output is linearized and the device further machined to tighter specifications which increases its accuracy and precision. To further determine the validity of this method for assessing edema, the half-time values from clinical studies can be correlated to the severity of edema as assessed by multiple clinicians. A preferred embodiment device can be miniaturized and the amount of applied pressure can be automated as shown in FIG. 2B. The processor and display can be incorporated into the device housing 100 to display numerical values indicative of the severity of edema. The data for a given patient can be acquired and stored electronically. The device 100 can be operated by a battery 140, has a display 110, buttons or other actuators 120 to control parameter selection and operation, small lights (LEDs) 125 to indicate status of measurement, displacement member 104 which can be displaced a distance 102 to a second position 106.

Figure 4:
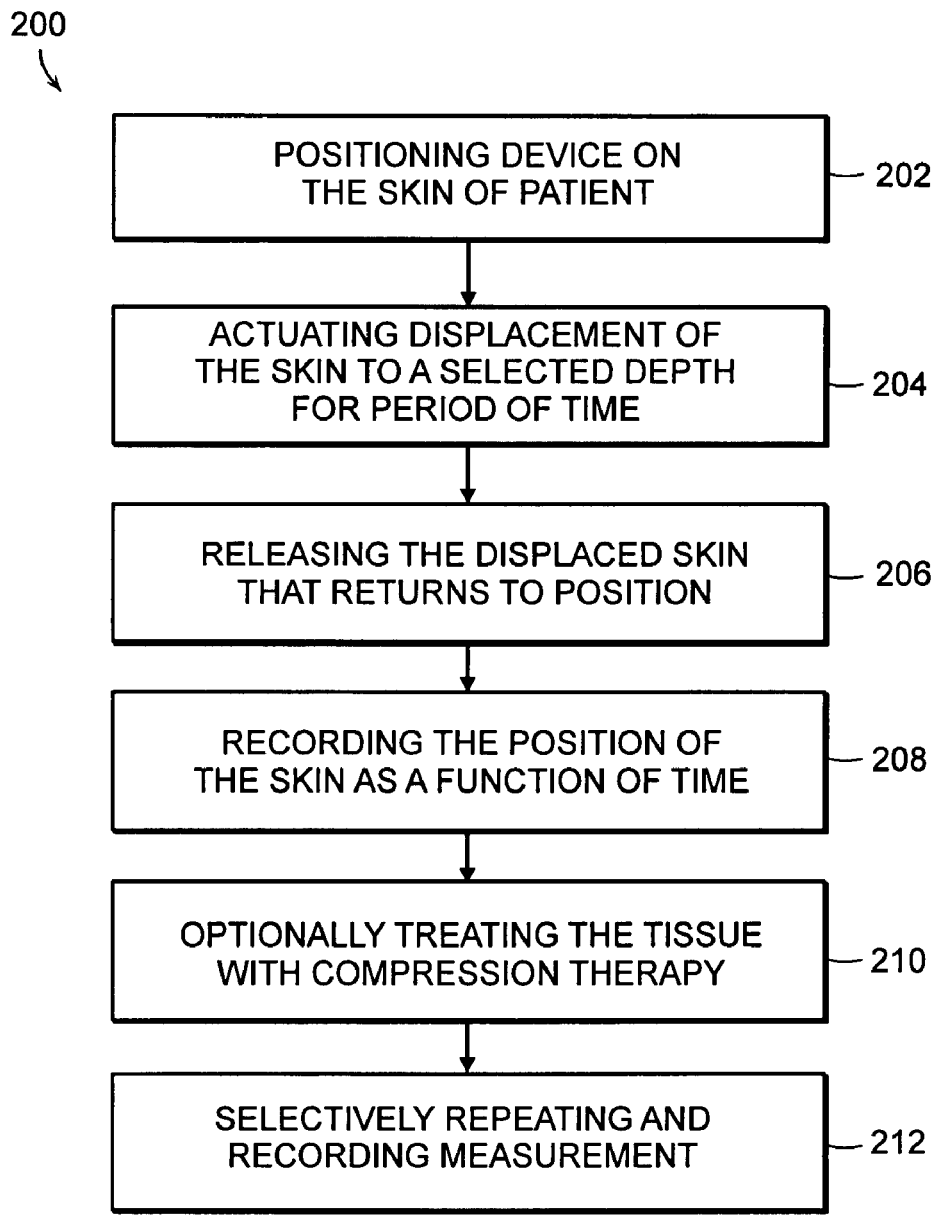
FIG. 4 illustrates a method of using the device to diagnose the condition of edematous tissue.

Illustrated in FIG. 4 is a process sequence illustrating a preferred method 200 of quantitatively measuring edema in accordance with the invention. After positioning the device 202 on the skin of the patient, the user either manually or electronically actuates the device to displace the skin and underlying tissue to a selected depth for a selected period of time 204. The user then releases the pressure exerted by the device which allows the tissue and skin to return 206 to a position. The device records the position of the skin as a function of time 208. The user can optionally treat the patient with compression therapy and/or medication 210. The user can also elect to repeat and record additional measurements 212.

The claims should not be read as limited to the described order or elements unless stated to that effect. Therefore, all embodiments that come within the scope and spirit of the following claims and equivalents thereto are claimed as the invention.

What is claimed is:

1. A method of measuring edema comprising:
   contacting a region of skin tissue of an arm or leg of a patient with a displacement member the region of tissue including edematous tissue;
   applying pressure to the region of skin tissue to displace the region of tissue a distance to a displaced position with the displacement member;
   releasing the pressure applied with the displacement member to the region of skin tissue;
   subsequently measuring a displacement of the region of tissue with the displacement member and a sensor that measures a displacement of the displacement member over a time during which the region of tissue relaxes from the displaced position; and
   displaying a quantitative value from the measured displacement with a display device, the measured displacement indicating a level of edema.

2. The method of claim 1 further comprising using the displacement member, a light source and a sensor, the light source and sensor determining a position of the displacement member.

3. The method of claim 2 further comprising using a housing on which the displacement member, light source and sensor are mounted.

4. The method of claim 1 further comprising measuring a time for return of the tissue to half the distance of the displaced position.

5. The method of claim 1 wherein the steps of contacting the region of tissue further comprises contacting a region of skin of the patient with the displacement member, displacing the region of skin with the displacement member and holding the displacement member at the displaced position for a selected period of time prior to the releasing step and subsequently measuring the relaxation of the skin from the displaced position.

6. The method of claim 1 further comprising treating the region of edematous tissue by compressing the region of tissue for a period of time.

7. The method of claim 1 further comprising recording the displacement of tissue as a function of time after the release of pressure.

8. The method of claim 1 further comprising using a housing, the housing and the displacement member undergoing relative movement from a first position to a second position.

9. The method of claim 1 further comprising comparing measured displacement data with stored data.

10. The method of claim 1 further comprising holding a housing on which the displacement member is mounted, and processing displacement data with a processor in the housing.

11. The method of claim 1 wherein the sensor comprises an LVDT such that the method further comprises using the LVDT to measure the displacement of the displacement member.

12. The method of claim 1 further comprising processing an output signal from the sensor with an amplification and filter circuit.

13. The method of claim 1 wherein the sensor and displacement member are mounted in a housing with a battery.

14. A method for measuring edema in an arm or leg of patient comprising:
   contacting a region of tissue on the arm or the leg of a patient with a displacement member, the region of tissue including edematous tissue;
   applying pressure to the region of tissue to displace the region of tissue a selected distance to a displaced position with the displacement member;
   releasing the pressure applied with the displacement member to the region of interest;
   subsequently measuring a displacement of the region of tissue from the displaced position with the displacement member and a sensor that measures a displacement of the displacement member over a period of time during relaxation of the edematous tissue from the displaced position; and
   displaying a quantitative value from the measured displacement with a display device, the measured displacement indicating a level of edema.

15. The method of claim 14 further comprising using a housing, the displacement member being movably attached to the housing.

16. The method of claim 14 further comprising measuring tissue swelling in the arm or leg of the patient.

17. The method of claim 14 further comprising treating the patient by compressing the region of tissue for a period of time and subsequently remeasuring edema in the region of tissue of the patient.

18. The method of claim 14 further comprising using a battery mounted within a housing to provide power to the sensor for measuring patient edema in the arm or the leg of the patient, the displacement member being mounted to the housing.

* * * * *